US008795293B2

(12) United States Patent
Petersen et al.

(10) Patent No.: US 8,795,293 B2
(45) Date of Patent: Aug. 5, 2014

(54) FLIPP TACK PUSHER (75) Inventors: Wolf Petersen, Berlin (DE); Thore Zantop, Muenster (DE)

(73) Assignee: Karl Storz GmbH & Co. KG (DE)

( * ) Notice: Subject to any disclaimer, the term of this patent is extended or adjusted under 35 U.S.C. 154(b) by 662 days.

(21) Appl. No.: 12/240,819

(22) Filed: Sep. 29, 2008

(65) Prior Publication Data
US 2010/0082045 A1 Apr. 1, 2010

(51) Int. Cl.
*A61B 17/10* (2006.01)

(52) U.S. Cl.
USPC .......................................... 606/139; 606/232

(58) Field of Classification Search
USPC .................................. 606/139, 232
See application file for complete search history.

(56) References Cited

U.S. PATENT DOCUMENTS

| 4,738,255 A * | 4/1988 | Goble et al. ................. 606/86 R |
| 5,217,486 A * | 6/1993 | Rice et al. ..................... 606/232 |
| 2005/0240227 A1 * | 10/2005 | Bonutti ........................ 606/232 |
| 2007/0016208 A1 | 1/2007 | Thornes |
| 2008/0234729 A1 * | 9/2008 | Page et al. ..................... 606/232 |

OTHER PUBLICATIONS

Minimally Invasive Coracoclavicular Ligament Augmentation With a Flip Button/Polydioxanone Repair for Treatment of Total Acromioclavicular Joint Dislocation, Mathias Wellmann, M.D., Thore Zantop, M.D., and Wolf Petersen, M.D. Anthroscopy. The Journal of Anthroscopic and Related Surgery, vol. xx, No. x (Month), 2007: pp. xxx, 5 pages.
American Journal of Sports Medicine http://ajs.sagepub.com Biomechanical Evaluation of Minimally Invasive Repairs for Complete Acromioclavicular Joint Dislocation—Mathias Wellmann, Thore Zantop, Andre Weimann, Michael J. Raschke and Wolf Petersen Am. J. Sports Med. 2007; 35; 955 originally published online Feb. 22, 2007; DOI: 10.1177/0363546506298585—8 pages.

* cited by examiner

*Primary Examiner* — Corrine M McDermott
*Assistant Examiner* — Son Dang
(74) *Attorney, Agent, or Firm* — St. Onge Steward Johnston & Reens LLC (57) ABSTRACT

A device for pushing an anchor through a bore in a bone is provided with an elongated shaft, an anchor carrying assembly disposed at a distal end of the shaft for carrying an anchor, and a plunger disposed in the elongated shaft. The plunger is movable relative to the elongated shaft. First, threads are attached to the anchor. Then, the anchor is positioned in the anchor fastener, and the elongated shaft is placed next to the bore in the bone. Next, the plunger is inserted into the elongated shaft, and a force is exerted to on the plunger to move it in direction of the distal end of the elongated shaft such that a distal end of the plunger comes into contact with the anchor and pushes the anchor through the bore in the bone.

7 Claims, 5 Drawing Sheets

FLIPP TACK PUSHER

FIELD OF THE INVENTION

The invention relates to medical devices and in particular to a medical instrument for pushing an implant or anchor through a bore in a bone.

BACKGROUND OF THE INVENTION

Acromioclavicular joint dislocations usually involve a severe displacement of the lateral end of the clavicle relative to the acromium of the scapula. Treatment of complete acromioclavicular joint dislocation is still very controversial. It ranges from rehabilitation to extensive surgical reconstruction. However, high-grade injuries (type IV, V, and VI) are typically treated surgically.

Most reconstruction techniques addressing these injuries selectively focus on coracoclavicular ligament augmentation because it has been shown a primary stabilizer of the acromioclavicular joint. The main problems in the clinical routine of coracoclavicular polydioxanone (PDS) loop augmentations are highly invasive preparation of the coracoid base and anterior subluxation of the clavicle causing malreduction of the acromioclavicular joint post operatively. Furthermore, the synthetic materials used for coracoclavicular cerclage have been detected to saw through the lateral clavicle and the coracoid as a result of rotational motion of the clavicle. On the other hand, rigid acromiclavicular joint fixation, using such techniques as the Bosworth screw or C-hook implants, leads to overstiffening of the joint and further complications, such as implant breakage and implant migration. A common disadvantage of all of these techniques is that they are highly invasive and are associated with corresponding postoperative morbidity.

Recently, minimally invasive arthroscopic techniques have been developed in order to reduce morbidity during the rehabilitation period and to improve surgical outcome. One advantage of suture anchors is that they can be placed at or close to the insertion site of the coracoclavicular ligaments. Therefore, the augmentation can imitate the course of the coracoclavicular ligaments more closely than can a PDS cerclage that is placed around the coracoid. However, most known suture anchors are primarily developed for connecting a soft tissue to a bone. In contrast, coracoclavicular augmentation means anchoring bone to bone. The length of the suture loop connecting both bones required for coracoclavicular ligament augmentation differs significantly from the direct bone to tendon contact achieved by other procedures. Furthermore, the coracoid suture anchor has to withstand much higher stress than the anchors used in other procedures.

A new technique that reduces the above complications by replicating the orientation of the native coracoclavicular ligament complex has been described in Wellmann, M., Zantop, T., Peterson, W., "Minimally Invasive Coracoclavicular Ligament Augmentation With a Flip Button/Polydioxanone Repair for Treatment of Total Acromioclavicular Joint Dislocation," *Arthroscopy* 2007, which is incorporated herein by reference. This technique provides a minimally invasive sub-coracoid and clavicular fixation of a double PDS loop by use of two flip buttons or anchors, typically used for extracortical anterior cruciate ligament graft fixation.

Metal anchors or buttons are commonly used for fixation of grafts during the anterior cruciate ligament reconstruction surgery. Usually, the ruptured ligament is removed and drill-holes are made into close vicinity of the original insertion cites of the anterior cruciate ligament. Then, a replacement graft, which can be either a natural or a prosthetic ligament, is pulled through and fixed into the drill-holes using the anchors, thus replacing the ruptured ligament. The common technique for moving the anchor though the drill-hole in the bone is to use a thread which is fixed to the anchor to pull the anchor out. Such technique has been described, for example, in U.S. Patent Application No. 2007/0016208 to Thornes. In the method disclosed in Thornes, a suture is passed upwards through a drill hole in a bone and then is passed through an open surgical wound. This pull-through suture, which engages an aperture of a button (anchor), can then advance the button through the drill-hole. The disadvantage of such method is that, in addition to a main incision through which the replacement graft with anchors is introduced, a second access is required in order to pass the anchor through the opening in the bone. Accordingly, such method is more invasive and, thus, more traumatic to a patient undergoing the procedure.

In view of the above described shortcomings of the prior art devices, there is a need for improved devices, instruments and surgical methods used in replacing and reconstructing torn or dislocated ligaments so as to make the process more efficient and effective, and, at the same time, less traumatic to the patient.

SUMMARY OF THE INVENTION

Accordingly, it is an object of the present invention to provide an improved device for moving an anchor through a bore in a bone to be used in ligament replacement or ligament reconstruction procedure that overcomes the deficiencies of the prior art.

In order to achieve at least some of the objects listed above, a device for pushing an anchor through a bore in a bone is provided, comprising an elongated shaft having an axis, a proximal end and a distal end, an anchor carrying assembly disposed at the distal end of the elongated shaft for carrying an anchor, and a plunger disposed in the elongated shaft, having a proximal end and a distal end. The plunger is movable relative to the elongated shaft and has a length that is substantially greater than a length of the elongated shaft such that when the plunger is moved within the elongated shaft, the distal end of the plunger extends outwardly beyond the distal end of the elongated shaft to push the anchor out of the distal end of the elongated shaft and into a bore in a bone.

In certain embodiments, the device may also have an anchor fastener disposed in the anchor carrying assembly formed as a cavity extending longitudinally along the axis of the elongated shaft for receiving the anchor.

In some embodiments, the anchor carrying assembly may have a groove positioned on one side of the anchor fastener for receiving threads attached to the anchor.

In certain embodiments, the distal end of the elongated shaft may have a beveled edge for positioning the anchor carrying assembly in the bore in the bone.

In some embodiments, the anchor fastener may be connected with the elongated shaft through an opening in the cavity. In certain of these embodiments, the distal end of the plunger may be engageable with the anchor by being displaced in direction of the distal end of the elongated shaft.

In some embodiments, the device may further comprise a handle disposed at the proximal end of the elongated shaft. In certain of these embodiments, the handle may be ergonomically shaped to facilitate gripping and maneuvering of the elongated shaft by a user.

In some embodiments, the device may also have a handle disposed at the proximal end of the plunger. In certain of these embodiments, the handle may be ergonomically shaped to facilitate gripping and maneuvering of the plunger by a user.

In some embodiments, the plunger may be positioned inside the elongated shaft through an opening at the proximal end of the elongated shaft.

In another embodiment, a device for pushing an anchor through a bore in a bone is provided, comprising an elongated shaft having an axis, a proximal end and a distal end, an anchor carrying assembly disposed at the distal end of the elongated shaft, comprising an anchor fastener formed as a cavity extending longitudinally along the axis of said elongated shaft and a groove arranged on one side of said anchor fastener, and a plunger moveably disposed in the elongated shaft, having a proximal end and a distal end. The plunger has a length that is substantially greater than a length of the elongated shaft such that when the plunger is moved within the elongated shaft, the distal end of the plunger extends outwardly beyond the distal end of the elongated shaft to push the anchor out of the distal end of the elongated shaft and into a bore in a bone.

The device further comprises an anchor releasably engaged in the anchor fastener, and threads attached to the anchor and positioned in the groove for retaining the anchor in the anchor fastener.

In some embodiments, the distal end of the elongated shaft has a beveled edge for positioning the anchor carrying assembly in the bore in the bone.

In some embodiments, the device also has a handle disposed at the proximal end of the elongated shaft. In certain of these embodiments, the handle is ergonomically shaped to facilitate gripping and maneuvering of the elongated shaft by a user.

In some embodiments, the device further has a handle disposed at the proximal end of the plunger. In certain of these embodiments, the handle is ergonomically shaped to facilitate gripping and maneuvering of the plunger by a user.

In some embodiments, the distal end of the plunger is engageable with the anchor by being displaced in direction of the distal end of the elongated shaft and being extended through an opening in said anchor fastener.

In yet another embodiment, a method for pushing an anchor through a bore in a bone is provided, including the steps of attaching threads to the anchor to be pushed, positioning the anchor in an anchor fastener disposed at a distal end of an elongated shaft, placing the distal end of the elongated shaft next to a bore in a bone, inserting a plunger into the elongated shaft, exerting a force on a proximal end of the plunger to move the plunger in direction of the distal end of the elongated shaft such that a distal end of said plunger comes into contact with the anchor disposed in said anchor fastener and then pushes said anchor through the bore in the bone, and pulling on the threads attached to the anchor to position the anchor in a position secured to the bone.

In certain embodiments, the plunger is inserted through an opening at the proximal end of the elongated shaft.

In some embodiments, the method also includes a step of retaining the anchor in the anchor fastener by holding the threads attached to the anchor.

In certain embodiments, the threads holding the anchor are released before the anchor is pushed through the bore.

In some embodiments, the threads attached to the anchor are arranged in a groove provided in the anchor fastener.

Other objects of the invention and its particular features and advantages will become more apparent from consideration of the following drawings and accompanying detailed description.

BRIEF DESCRIPTION OF THE DRAWINGS

Those skilled in the art will recognize that the embodiments illustrated in FIGS. 1-4 are not necessarily to scale.

DETAILED DESCRIPTION OF THE INVENTION

The present invention provides a device for use in a ligament reconstruction surgery, such as replacement of the coraclavicular ligament located in the human acromioclavicular shoulder joint. It should be understood, however, that the application of the present invention is not limited to such ligament and can be used for the replacement or reconstruction of any torn ligaments in a human body.

In FIGS. 1-4, a device for pushing an anchor through a bore in a bone is designated in its entirety by reference number 15.

Figure 1:
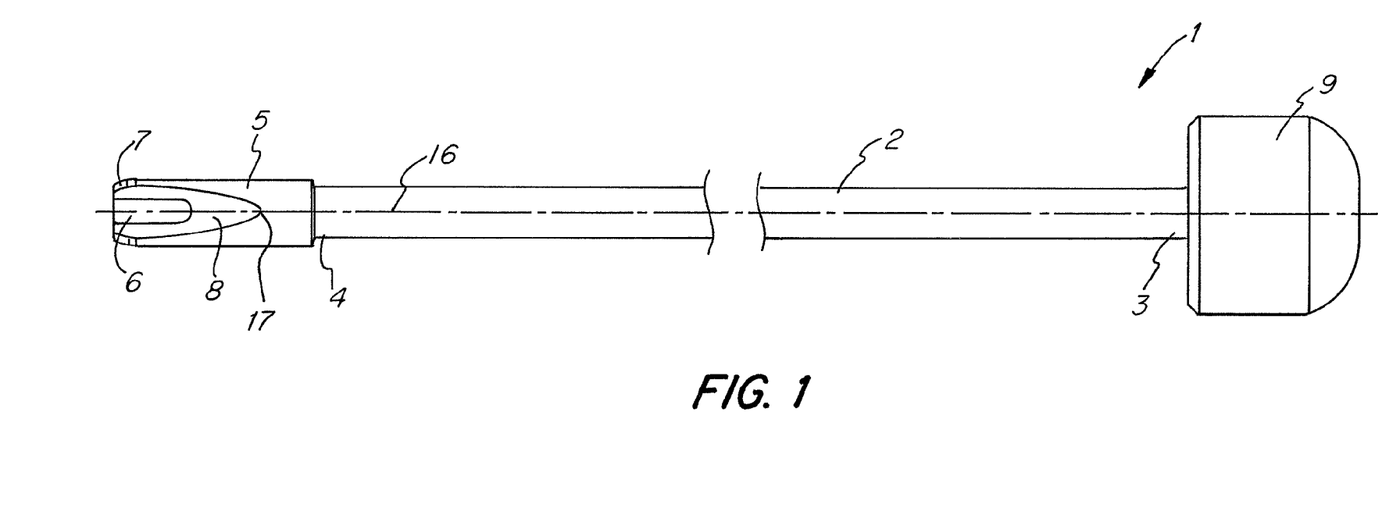
FIG. 1 is a top view of an elongated shaft portion of a device for pushing an anchor through a bore in a bone in accordance with one embodiment of the invention.

Referring to FIG. 1, an elongated shaft 1 of the device for pushing the anchor through the bore in the bone is shown. The shaft 1 has an elongated, roughly cylindrical body 2, which is hollow inside. A proximal end 3 of the elongated shaft 1 is provided with a handle 9. Since a ligament replacement or reconstruction procedure, like any surgical procedure, requires great accuracy and precision, the handle 9 is shaped such as to facilitate gripping of the proximal end 3 of the elongated shaft 1 by a surgeon and maneuvering of the elongated shaft 1 inside a patient's body.

At a distal end 4 of the elongated shaft 1, an anchor carrying assembly 5 is disposed. The anchor carrying assembly 5 has an anchor fastener 6 provided at the distal end of the assembly. The anchor fastener 6 is formed as a cavity that extends along a longitudinal axis 16 of the elongated shaft 1 and that is contoured to precisely fit the anchor that is being pushed through the bone tunnel. Although the cavity illustrated in FIG. 1 is arranged to fit an anchor having a roughly oval shape, it should be understood that the cavity of the anchor fastener 6 can be made to fit various shapes and sizes of the bone anchors.

The edge 7 of the anchor carrying assembly 5 disposed at the distal end 4 of the elongated shaft 1 is beveled to provide for an improved attachment of the device to the bone tunnel. Because a diameter of the anchor carrying assembly 5 is approximately equal to a diameter of the tunnel drilled in the bone, when the device is brought to the bone tunnel, the beveled portion 7 of the device fits inside the tunnel, thus ensuring a tight fit between the device and the bone tunnel.

A groove 8 is formed from the distal end of the anchor carrying assembly 5 to a point 17 at a certain distance from the proximal end of the anchor carrying assembly 5. The side walls of the groove 8 extend outwardly from the point 17 toward the beveled edge 7 of the anchor carrying assembly 5. The length of the groove 8 is preferably greater than the length of the opening of the anchor fastener 6. This groove 8 serves to allow threads attached to the anchor to be fitted onto the device when the device is inserted into the bone tunnel, as is described in more detail below.

Figure 2:
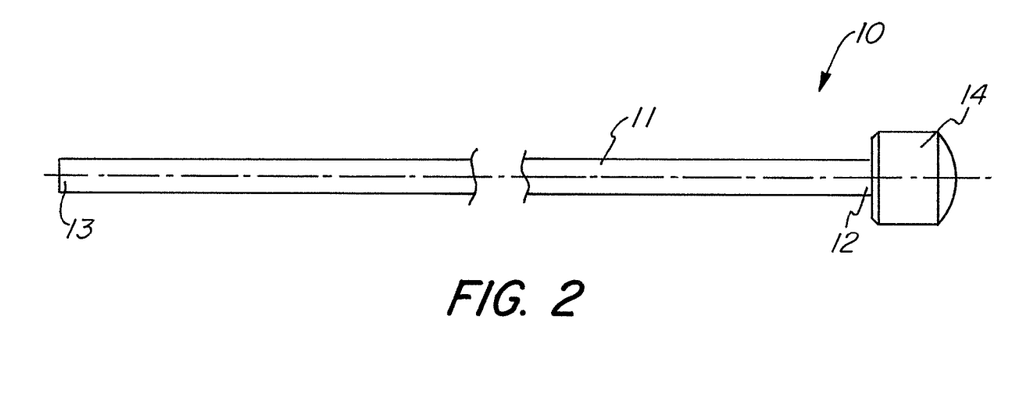
FIG. 2 is a top view of a plunger portion of the device for pushing the anchor through the bore in the bone of FIG. 1.

Referring now to FIG. 2, a plunger 10 of the device for pushing the anchor through the bore in the bone is shown. The plunger 10 is formed as a solid rod that is substantially circular in a cross-section, having a proximal end 12 and a distal end 13. The diameter of the cross-section of the plunger 10 is less than the diameter of the hollow portion of the elongated shaft 1, so that the plunger 10 fits inside the elongated shaft 1. The plunger 10 has a handle 14 disposed at the proximal end 12, having a rounded shape. As described above, such design of the handle 14 allows for an easy gripping and maneuvering of the plunger 10 by the surgeon.

Figure 3:
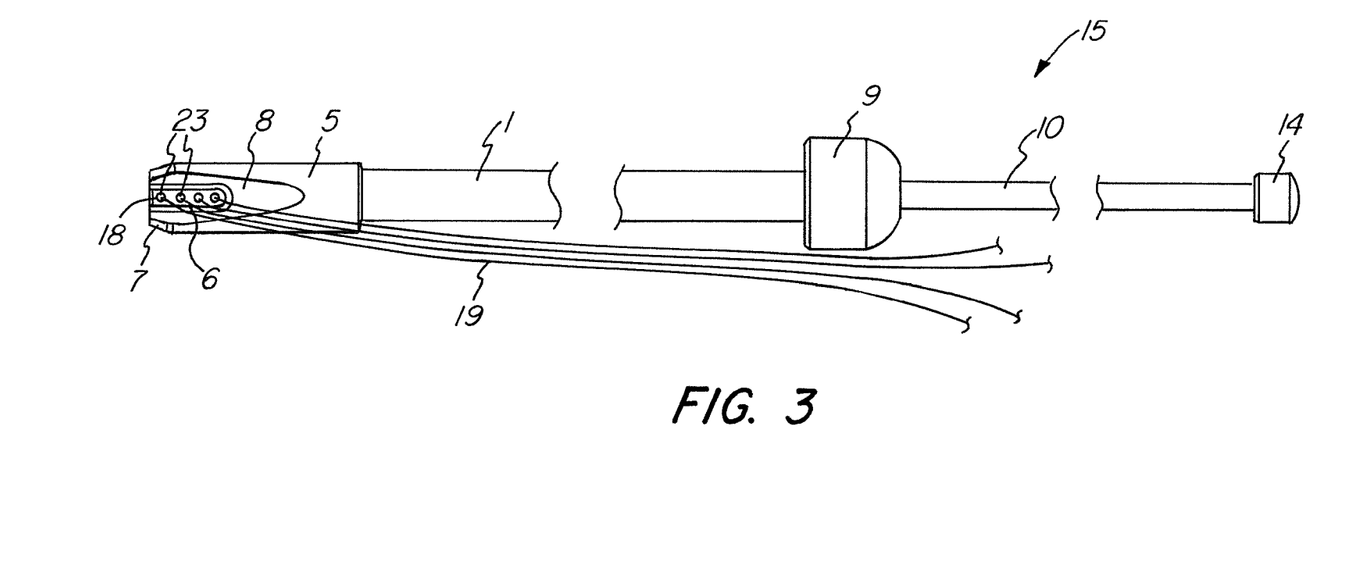
FIG. 3 is a top view of the device for pushing the anchor through the bore in the bone shown in FIGS. 1 and 2.

Referring now to FIG. 3, the whole device 15 of the present invention is shown. As shown in FIGS. 1-2, the device 15 has the elongated shaft 1 that is formed as a hollow cylindrical body. The elongated shaft 1 has a handle 9 disposed at the proximal end of the shaft 1, having a rounded shape such as to assist in gripping and maneuvering of the device 15 by a surgeon during the ligament replacement procedure. The beveled edge 7 extends along the circumference of the distal end of the elongated shaft 1 to allow for a precise fitting of the elongated shaft 1 within the bore 21 in the bone 22, as further illustrated in FIGS. 4A-4C.

The anchor carrying assembly 5 is disposed at the distal end of the elongated shaft 1. The anchor carrying assembly 5 includes an anchor fastener 6 that extends in the longitudinal direction of the anchor carrying assembly 5 and is designed as a longitudinally extending cavity. The shape of the cavity forming the anchor fastener 6 is preferably designed to correspond approximately to the contour of the anchor that is positioned in the anchor fastener such that the anchor can be releasably but securely fixed within the cavity of the anchor fastener 6. Additionally, the anchor carrying assembly 5 includes a groove 8 arranged on one side of the anchor fastener 6.

The device 15 further includes the plunger 10 formed as a round solid rod. The proximal end of the plunger 10 has a handle 14 via which the plunger 10 can be gripped by hand by the surgeon operating it. The plunger 10 is shown as fitted inside the hollow space of the elongated shaft 1, which extends along the longitudinal axis of the shaft 1 starting from the proximal end of the shaft through the distal end of the shaft. The overall length of the plunger 10 is substantially greater than then the length of the elongated shaft 1, so that when the plunger 10 is inserted and pushed into the elongated shaft 1, the distal end of the plunger 1 extends outwardly beyond the distal end of the elongated shaft 1. Specifically, the length of the plunger 10 must be sufficient relative to the length of the elongated shaft 1 to allow the distal end of the plunger 10 to move the anchor 18 through the entire length of the bore 21 such that the anchor is pushed out from the bore 21 on the opposite end of the bore.

The plunger 1 is inserted into an opening formed in the handle 9 at the proximal end of the elongated shaft 1. The distal end of the plunger 10 can then be engaged with the anchor 18 fixed within the anchor fastener 6 by being displaced in the direction of the distal end of the elongated shaft 1 until the distal end of the plunger 10 comes in contact with the anchor 18. The cavity of the anchor fastener 6 is connected with hollow space of the elongated shaft 1 through an opening formed in the anchor fastener 6 (not shown). This way, when the plunger 10 is moved toward the distal end of the elongated shaft 1, the distal end of the plunger 1 travels through the hollow space within the elongated shaft 1 into the opening in the anchor fastener 6, abuts the anchor 18 retained in the anchor fastener 6, and begins to push the anchor 18 out of the anchor carrying assembly 5 through the open end at the distal end of the assembly. The anchor 18 can thus be pushed through the bore 21 by applying a force to the proximal end of the plunger 10, for example by using a surgical hammer.

FIG. 3 also shows an anchor 18, which is fitted into the cavity of the anchor fastener 6. The anchor 18 illustrated in FIG. 3 is a flip button manufactured by Karl Storz GmbH & Co. in Germany that is typically used for extracortical anterior cruciate ligament graft fixation. The anchor 18 has an oblong body with rounded edges, and has four apertures 23 formed along a longitudinal axis of the anchor for attachment of threads. However, it should be understood that any known kind of anchor can be used in accordance with the present invention, depending on a type of procedure performed.

Irrespective of which type of the bone anchor is used, the ends of the threads 19 are secured to the anchor 18 by intertwining them within the apertures 23 formed in the anchor 18. The threads 19 are threaded through the groove 8 in the anchor carrying assembly 5 before the device 15 is inserted into the bore in the bone so that, despite the tight fit between the distal end of the elongated shaft 1 and the bore 21, the threads 19 can freely extend out of the bore 21 through the groove 8.

In order to ensure that the anchor 18 remains securely positioned within the anchor carrying assembly 5 while the device 15 is brought to the bore 21 in the bone 22, the threads 19 attached to the anchor 18 are maintained in a tense position, thus retaining the anchor 18 within the anchor fastener 6.

It should be noted that the elongated shaft 1, the plunger 10 and the anchor carrying assembly 5 can be made with any common surgical instrument materials, such as titanium or the like, known to those of skill in the art. Likewise, the threads 19 may be any surgical threads known in the art that are suitable for a particular procedure being performed.

Figure 4A:
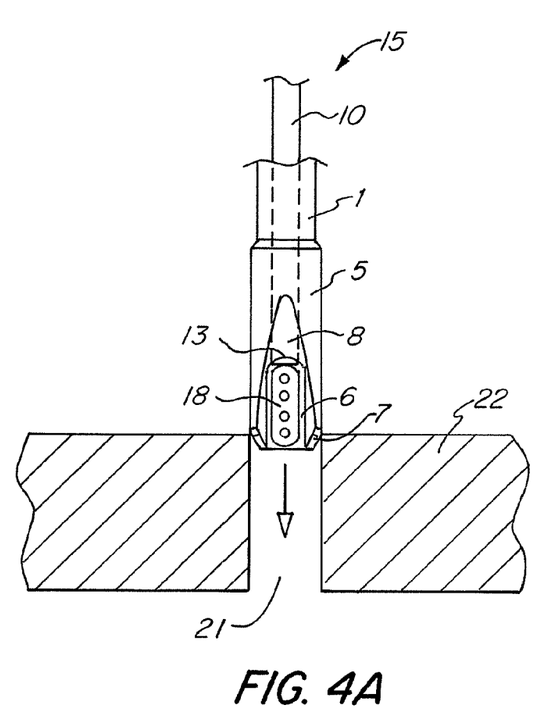
FIG. 4A shows, as a schematic view, how the device of FIGS. 1-3 is assembled and brought to the bore in the bone.
Figure 4B:
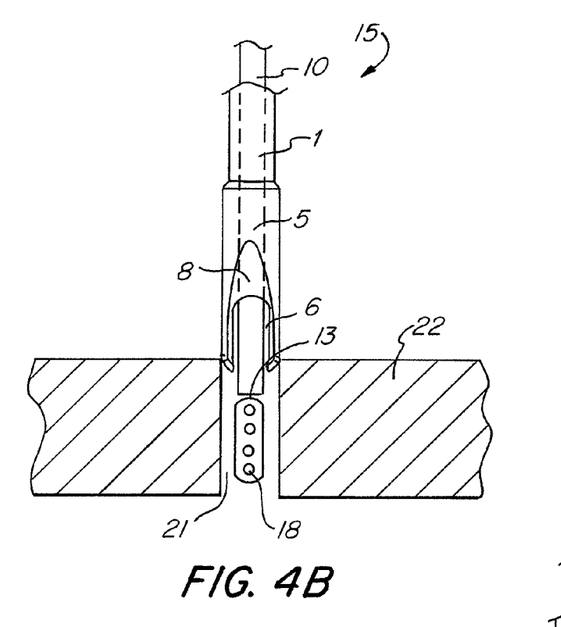
FIG. 4B shows, as a schematic view, how the device of FIGS. 1-3 engages the anchor and pushes the anchor through the bore.
Figure 4C:
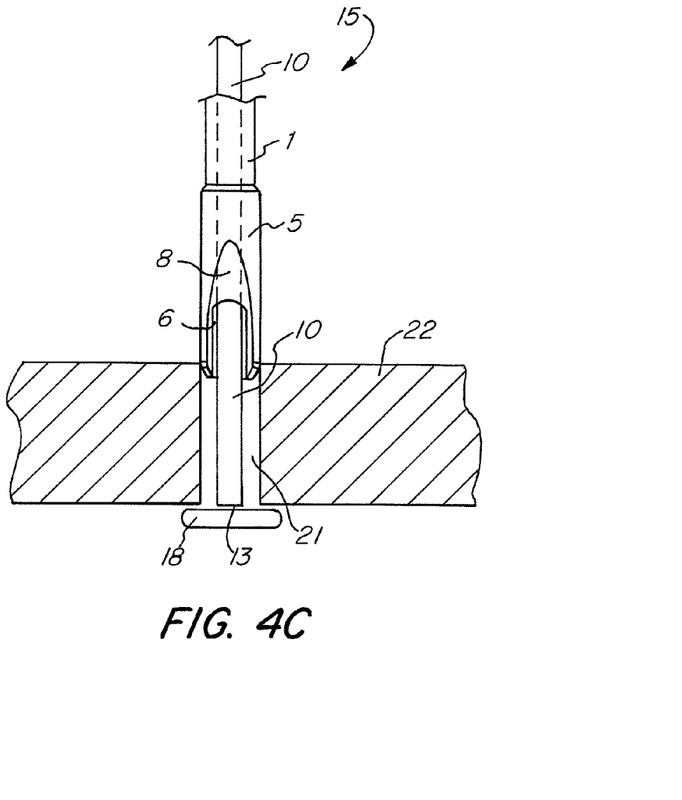
FIG. 4C shows, as a schematic view, the anchor being pushed completely through the bore by the device of FIGS. 1-3 and being positioned securely on the other side of the bone.

FIGS. 4A-4C illustrate the steps of the operating technique in which the anchor is pushed through a bore in a bone by employing the device according to the present invention.

In the illustrative embodiment in FIG. 4A, an opening 21, for example a bore, has been formed in a bone 22 in the area of tissue detachment by using a surgical drill. The drilling can be performed by any methods known to those skilled in the art. The internal diameter of the bore 21 formed is approximately equal to the external diameter of the distal end of the anchor carrying assembly 5, but is slightly larger than the external diameter of the beveled edge 7 of the assembly 5. Thus, when the distal end of the anchor carrying assembly 5 is brought to the bore 21 in the bone 22, the slightly smaller diameter of the beveled edge 7 allows the edge 7 fit tightly inside the bore 21, providing for secure positioning of the device 15 on the bone 22.

The anchor 18 is fitted within the cavity of the anchor fastener 6 before the device 15 is brought to the bone tunnel. As illustrated in FIG. 3, the groove 8 formed in the anchor carrying assembly 5 allows the threads 19 attached to the anchor 18 to be freely extended out from the groove 8, while the elongated shaft 1 with the anchor 18 is securely positioned within the bore 21. Thus, the anchor 18 is held in place within the anchor fastener 6 by pulling at the threads 19.

Once the anchor carrying assembly 5 with the anchor 18 is brought to the bone 21, the plunger 10 is inserted into the opening at the proximal end of the elongated shaft 1 (not shown). Then, the surgeon releases the threads 19 and pushes the plunger 10 through the hollow space of the shaft 1, shown in phantom lines, in the downward direction indicated by an arrow until the distal end 13 of the plunger 10 comes out from the opening in the anchor fastener 6 and comes into contact with the anchor 18, as shown in FIG. 4A. As described above, the plunger is moved through the shaft by applying force to the proximal end of the plunger, either manually or by use of another device, such as hammer.

FIG. 4B shows the anchor 18 being pushed part-way through the bore 21. The distal end 13 of the plunger 10 extends beyond the distal end of the elongated shaft 1 and into the bore 21 in the bone 22. The anchor 18 is thus advanced substantially longitudinally through the bore 21.

FIG. 4C illustrates the anchor 18 being pushed completely through the bore 21 and being positioned securely on the other side of the bone 22. In this position, the distal end 13 of the plunger 10 is roughly aligned with the surface of the bone 22. The anchor 18 is displaced out of the bore 21 and is positioned on the other side of the bone 22, opposite from the bore opening where the anchor carrying assembly 5 is inserted. The plunger 10 is allowed to rest in this position, and the free ends of the threads 19 that are still attached to the anchor 18 and extended through the bore 21 and out of the groove 8, are picked up by the surgeon and tightened. By tightening the threads 19, the anchor 18 is tilted relative to its longitudinal position within the bore 21 and is positioned so that the anchor 18 is now laying on the bone 22. The plunger 10 and the elongated shaft 1 with the anchor carrying assembly 5 are then retracted from the bore 21, and the threads 19 secured in the bone 22 by the anchor 18 are used for connection to another bone or to a replacement ligament.

The device for pushing the anchor through the bore in the bone provided by the present invention thus presents an improved device for use in a ligament replacement or ligament reconstruction surgery that allows for more effective and less traumatic method of inserting and securing the anchor in the bone.

The following describes an exemplary procedure for treatment of acromioclavicular joint disruption, using the device of the present invention.

Procedure Set-Up:

The patient is placed in the beach-chair position, and the upper extremity is draped in a manner to allow full and unrestricted arm positioning during the procedure. Then an oblique 3-cm skin incision toward the coracoid tip, starting at the posterior edge of the lateral clavicle, is made. The torn fascia of the deltoid muscle is further open along its fiber course, and the superior aspect of the distal clavicle and the acromioclavicular joint line are exposed by blunt subfascial dissection. The clavicular insertions of the trapezoid and deltoid ligament are palpated at the anteroinferior surface of the clavicle, and the center between them is marked on the upper clavicular surface with a curette. If palpation of the ligament stumps is not possible, the conoid tubercle alternatively serves as an orientation mark. Depending on the individual shoulder proportions, the center of the coraclavicular ligament attachment is located approximately 30 mm medial to the acromioclavicular joint line. Blunt preparation is further performed toward the coracoid process, until the base can be palpated.

Preparation of Bone Tunnels:

The base of the coracoid must be identified to place a C-shaped drill guide beyond it. The drill guide is introduced to the medial coracoid aspect, whereas the lateral aspect should not be approached, leaving the coracoid ligament intact. The drill guide is slightly moved under the coracoid to control the strictly proximal position at the coracoid base. By use of the C-shaped drill guide, a K-wire is paced centrally in the coracoid base and overdrilled with a 4.5-mm drill bit. Then the anatomically placed clavicular bone tunnel is drilled in the preassigned central zone of the trapezoid and conoid ligament. This bone tunnel is placed slightly anterior to the long axis of the clavicle. The sharp cortical edges of the drill hole are smoothed with a curette.

Placement of Buttons:

A 0.7-mm doubled PDS suture is intertwined between two flip button, normally used for extracortical anterior cruciate ligament graft fixation. For this connection, the PDS cerclage is used via the flip buttons through their internal eyelets in a lifting block fashion. The distal button is then inserted into the device of the present invention, is guided through the 4.5-mm coracoid bone channel in an upstanding position, and placed under the coracoid base, as illustrated in FIGS. 4A-4C and described above. Afterwards, the button is flipped into a horizontal position by pulling the PDS loop. Subsequently, a suture lasso is guided through the clavicle bone tunnel by use of crochet hook-shaped instrument. Consequently, the clavicular flip button with the free ends of the double PDS loop is retrieved through the clavicular drill hole after it is fed into the suture lasso. The superclavicular flip button is advanced to the upper clavicle surface by pulling the free ends of the double PDS loop. Before definitive repositioning, the prevalently ruptured acromioclavicular joint disk is resected or sutured. By use of an anatomic offset repositioning instrument, the clavicle is reduced in the acromioclavicular joint afterward.

Wound Closure:

The PDS loop is tied via a surgeon's knot, followed by three square knots. If possible, the torn acromioclavicular ligaments are adapted by use of a No. 2 PDS suture. The deltoid fascia and subcutaneous tissue are carefully adapted. Skin closure is performed with a No. 4 Monocryl stitch via an intracutaneous suture technique.

Post-Operative Rehabilitation:

The upper extremity is immobilized for four weeks in 30 degrees of abduction and neural rotation. During this period, rehabilitation with passive controlled arm movement is accomplished. Afterwards, the free motion of the shoulder is liberalized.

Although the invention has been described with reference to a particular arrangement of parts, feature and the like, these are not intended to exhaust all possible arrangement of features, and indeed many other modifications and variations will be ascertainable to those of skill in the art.

What is claimed is:

1. A device for pushing an anchor through a bore in a bone, comprising:
    an elongated shaft having an axis, a proximal end and a distal end;
    an anchor carrying assembly disposed at the distal end of said elongated shaft, comprising an anchor fastener formed as a cavity extending longitudinally along the axis of said elongated shaft and a groove arranged on one side of said anchor fastener; and beginning at a distal end of said anchor carrying assembly;
    an anchor releasably engaged in said anchor fastener such that the anchor does not extend beyond the distal end of the anchor carrying assembly when received therein;
    threads attached to said anchor and positioned in said groove for retaining the anchor in the anchor fastener;
    a plunger disposed in said elongated shaft, having a proximal end and a distal end;
    wherein said plunger is movable relative to said elongated shaft; and
    wherein said plunger has a length that is substantially greater than a length of said elongated shaft such that when the plunger is moved within the elongated shaft, the distal end of the plunger extends outwardly beyond the distal end of the elongated shaft to push said anchor out of the distal end of said elongated shaft and into a bore in a bone.

2. The device according to claim 1, wherein the distal end of said elongated shaft comprises a beveled edge for positioning said anchor carrying assembly in the bore in the bone.

3. The device according to claim 1, further comprising a handle disposed at the proximal end of said elongated shaft.

4. The device according to claim 3, wherein said handle is ergonomically shaped to facilitate gripping and maneuvering of said elongated shaft by a user.

5. The device according to claim 1, further comprising a handle disposed at the proximal end of said plunger.

6. The device according to claim 5, wherein said handle is ergonomically shaped to facilitate gripping and maneuvering of said plunger by a user.

7. The device according to claim 1, wherein the distal end of said plunger is engageable with the anchor by being displaced in direction of the distal end of said elongated shaft and being extended through an opening in said anchor fastener.

* * * * *